United States Patent [19]

Joiner

[11] Patent Number: 5,037,648

[45] Date of Patent: Aug. 6, 1991

[54] SKIN CONDITIONING PREPARATION HAVING A PH ABOVE 7, METHOD AND METHOD OF MAKING

[76] Inventor: Evelyn S. Joiner, 3880 S. Hillcrest Dr., Denver, Colo. 80237

[21] Appl. No.: 468,088

[22] Filed: Jan. 22, 1990

Related U.S. Application Data

[63] Continuation-in-part of Ser. No. 438,236, Nov. 20, 1989, abandoned.

[51] Int. Cl.$^5$ .................... A61L 9/04; A61K 31/78; A01N 59/00
[52] U.S. Cl. ........................ 424/81; 424/44; 424/683; 424/717; 424/684; 424/722; 514/554; 514/63
[58] Field of Search ............... 424/717, 81, 127, 44

[56] References Cited

U.S. PATENT DOCUMENTS

| | | | |
|---|---|---|---|
| 1,022,627 | 4/1912 | Hempel | 424/161 |
| 3,993,751 | 11/1976 | Zinke | 424/717 |
| 4,107,333 | 8/1978 | Hercelin | 424/47 |
| 4,666,707 | 5/1987 | Eguchi | 424/44 |

OTHER PUBLICATIONS

Drug and Cosmetic Ind., Dec. 1961, vol. 89, No. 6, pp. 718, 720, 804.

*Primary Examiner*—Thurman K. Page
*Assistant Examiner*—Peter F. Kulkosky
*Attorney, Agent, or Firm*—Fields, Lewis, Pittenger & Rost

[57] ABSTRACT

A skin conditioning composition in the form of a lotion applied to the skin has bicarbonate ions in an emollient carrier and pH in excess of 7.0. The composition is formed by the combining of a diluent with thickener/stabilizer and a humectant with a fat agent and emulsifier which brings the pH to 7.0 and above 7.0 to which is added an aqueous solution of sodium bicarbonate. A quantity of mineral oil which serves as an emollient is a preferred addition to the final mixture.

14 Claims, No Drawings

SKIN CONDITIONING PREPARATION HAVING A PH ABOVE 7, METHOD AND METHOD OF MAKING

This application is a continuation-in-part of application Ser. No. 438,236, filed Nov. 20, 1989, now abandoned.

TECHNICAL FIELD

This invention relates to a novel and improved skin preparation and a novel and improved method of improving the condition of the skin.

BACKGROUND ART

The skin is a busy frontier that mediates between the body organism and the environment. The color, texture, odor, and moisture condition of the skin vary considerably. Only water will plasticize the outer layer of the epidermis to give a softer, smoother skin. Cosmetic creams, lotions, oils have been utilized to soften the outer layer or epidermis of the skin and prevent escape of moisture. Damaged skin is usually manifested by dryness. Dry skin is caused by prolonged exposure to low humidity and air movement and/or by chemical changes due to aging or continual degreasing. The removal of oil from the skin causes a tendency for the pH of the skin to lean toward acidity. Skin that has been stressed can be simply dry with varied degrees of roughness. Fissures may also be present in the skin.

Some attempts have been made to enhance the condition of the skin by adding microscopic bubbles of carbon dioxide ($CO_2$) to a skin preparation such as is described in Heath U.S. Pat. No. 1,494,544. Hempel U.S. Pat. No. 1,022,627 and Great Britain Patent No. 776,293 disclose medicinal and therapeutic baths prepared by adding sodium bicarbonate to water.

DISCLOSURE OF INVENTION

A skin conditioning preparation and method disclosed has bicarbonate ions in an emollient carrier that are applied to the skin. The preparation is made by mixing a thickener/stabilizer in a diluent and adding a humectant in a first part, heating the first part and heating a second part which is primarily a fat agent, adding a third part to the first and second parts, the third part including an emulsifying agent which increases the pH and adding an aqueous saturated solution of sodium bicarbonate which forms bicarbonate ions in an emollient carrier.

DETAILED DESCRIPTION

As used herein, the following terms are defined as:

occlusion—reducing the rate of transepidermal water loss.

humectant—a substance that absorbs or helps another substance retain moisture such as glycerol or other polyhydric alcohols.

emulsifier—that which makes into an emulsion which is any colloidal suspension of a liquid in another liquid.

emollient—a substance having the power of softening or smoothing.

diluent—serving to dilute or make a liquid thinner.

opalescence—to exhibit a play of colors like that of the opal having a milky iridescence.

The starting material used for making a skin conditioning preparation according to the present invention is a first part (Part A) which includes a diluent, humectant and thickener/stabilizer which is mixed and heated to a selected temperature. A fat agent (Part B) is heated to a selected temperature. The two parts are mixed. An emulsifier (Part C) is added to emulsify and increase the pH and the three components are mixed and allowed to cool. An aqueous saturated solution of sodium bicarbonate ($NaCHO_3$) (Part D) is added when the temperature is about 55°-60° C. and all of these components are mixed to form bicarbonate ions in an emollient carrier which is in the form of a lotion that may be applied to the skin.

The following examples have been found suitable for carrying out the present invention:

EXAMPLE 1

| Part | Ingredients | % by Wt. | Function |
|---|---|---|---|
| A | Water | 84% | Diluent |
|  | Glycerin | 4% | Humectant |
|  | Polyacrylic acid (Carbopol ® 934 B.F. Goodrich) | .15% | Thickener/stabilizer |
|  | Bentonite | .13% | Thickener/stabilizer |
| B | Mineral Oil (Fat agent) | 6% | Emollient/moisture barrier |
|  | Glyceryl sterate | 1.7% | Opalescence agent/ moisture barrier |
|  | Stearic acid | 0.5% | Surfactant |
|  | Dimethicone* (Polydimethylsiloxane polymer 200 ® Fluid Dow Corning) | 0.5% | Moisture barrier/ emollient |
| C | Triethanolamine (T.E.A.) | q.s. to bring pH to slightly above 7.0 | Emulsifier |
| D | Aqueous saturated solution of sodium bicarbonate ($NaHCO_3$) at room temperature. | 1.3% |  |
| E | Mineral Oil | 1.0% | Emollient |
| F | Alkaline stable fragrance + preservatives | q.s. |  |

*Heat some aqueous saturated solution sodium bicarbonate to near boiling, about 50-60° C. Remove from heat and add some dimethicone. Stir until it ceases to bubble.

A preferred method of making the above Example 1 is as follows:

1. Mix bentonite and polyacrylic acid together and gradually mix into water then stir in the glycerin.
2. Heat parts A and B in separate containers to about 75° C. and mix together stirring continuously.
3. Add Part C.
4. Parts A, B and C should be mixed together quickly while they are very hot.
5. Continue stirring until temperature is down to about 55°-60° C.
6. Add Part D (sodium bicarbonate solution) and continue stirring until cool.
7. Add Part E and mix thoroughly. Add alkaline stable preservatives and fragrance as desired.

The above procedure and ingredients will make a skin lotion or cream that has the bicarbonate ion ($HCO_3^-$) in a stable solution supplying a hydroxyl ion ($OH^-$), available for bonding with the proton ($H^+$) in an acidic, dry, rough skin surface along with the replacement oil needed for a smooth healthy body surface. The chemical equation for the reaction for the aqueous saturated solution is:

$$NaHCO_3 + H_2O \rightarrow HCO_3^- + Na^+ + H_2O$$

The chemical equation for what takes place on the skin surface may be expressed as:

$$Skin\ H^+ + HCO_3^- \rightarrow Skin\ H_2O + CO_2$$

EXAMPLE 2

A second example would be identically the same as Example 1 but reducing the mineral oil to 4% by weight and adding white petrolatum of 2% by weight to Part B. The procedure for making Example 2 is the same as Example 1.

A primary objective of the present invention is to supply bicarbonate ions in a stable milieu that will also replace the oily film that is present on healthy skin. The beneficial results achieved by the skin preparation with composition above described include the formation of a water molecule in the cells of the skin thus overcoming dryness and roughness, removal of fissures, and the skin becomes smoother and a satiny feeling is achieved.

Although the present invention has been described with a certain degree of particularity, it is understood that the present disclosure has been made by way of example and that changes in details of structure and components may be made without departing from the spirit thereof.

What is claimed is:

1. A skin conditioning preparation that is applied directly to the skin surface of a dry skin comprising: bicarbonate ions in an emollient carrier to provide a mixture having a pH in excess of 7.0, said emollient carrier having a major portion of a water diluent and a humectant in the amount of about 4% by weight and a fat agent in the amount of about 6% by weight.

2. A skin conditioning preparation that is applied directly to the skin surface of a dry skin comprising a fat agent in the amount of about 6% by weight, a humectant in the amount of about 4% by weight, a major portion of a water diluent forming a mixture having a pH that is 7.0 and in excess of 7.0 to provide an emollient carrier and an aqueous saturated solution of sodium bicarbonate to provide bicarbonate ions in the emollient carrier to bring the mixture of bicarbonate ions in the emollient carrier to a pH of 7.0 and above 7.0.

3. A skin conditioning preparation that is applied directly to the skin surface of a dry skin consisting essentially of a first part having a major portion of water diluent and a humectant in the amount of about 4% by weight, a second part that is primarily a fat agent in the amount of about 6% by weight, a third part including triethanolamine in an amount to make the pH of a mixture of said first, second and third parts is 7.0 and in excess of 7.0 and a fourth part including an aqueous saturated solution of sodium bicarbonate.

4. A skin conditioning preparation as set forth in claim 3 wherein said second part includes mineral oil of about 4% by weight and white petrolatum of about 2% by weight.

5. A skin conditioning preparation that is applied directly to the skin surface of a dry skin consisting essentially of a first part including water of about 84% by weight, polyacrylic acid resin of about 0.15% by weight and bentonite of about 0.13% by weight, a second part including mineral oil of about 6% by weight, glyceryl sterate of about 1.7% by weight, stearic acid of about 0.5% by weight, and dimethicone of about 0.5% by weight, a third part including triethanolamine in an amount to make the pH of a mixture of said first, second and third parts of 7.0 and in excess of 7.0 and a fourth part including an aqueous saturated solution of sodium bicarbonate of about 1.3% by weight.

6. A skin conditioning preparation as set forth in claim 5 wherein said polyacrylic acid resin is Carbopol ®934 which serves as a thickener/stabilizer.

7. A skin conditioning preparation as set forth in claim 5 wherein said mineral oil serves as an emollient/moisture barrier.

8. A skin conditioning preparation as set forth in claim 5 wherein said first part includes glycerin in the amount of about 4% by weight which serves as a humectant.

9. A skin conditioning preparation as set forth in claim 1 further including the final addition of mineral oil of about 1% by weight and alkaline stable fragrance and preservatives.

10. A skin conditioning method comprising the step of:
applying bicarbonate ions in am emollient carrier having a pH in excess of 7.0 directly to the skin surface of a dry skin, said emollient carrier having a major portion of a water diluent and a humectant in the amount of about 4% by weight and a fat agent in the amount of about 6% by weight.

11. A method of making a skin preparation that is applied directly to the skin surface of a dry skin which comprises the steps of:
mixing two thickener/stabilizer ingredients in a diluent of water which is a major portion and stirring in a humectant in the amount of about 4% by weight to provide a first part,
heating said first part to a selected temperature,
heating a second part including a fat agent in the amount of about 6% by weight to a selected temperature,
mixing said first and second parts together,
adding a third part including an emulsifier to the heated first and second parts and heating and stirring the mixture for a selected time period, and
adding a fourth part including an aqueous saturated solution to said first, second and third parts and mixing to provide bicarbonate ions in an emollient carrier having a pH greater than 7.0.

12. A method of making a skin preparation that is applied directly to the skin surface of a dry skin comprising the steps of:
heating a first part including a water diluent, glycerin, polyacrylic acid, and bentonite to a temperature of about 75° C., said water being a major portion, said glycerin being in the amount of about 4% by weight,
heating a second part including mineral oil in the amount of about 6% by weight, and minor portions of glyceryl sterate and stearic acid to a temperature of about 75° C.,
mixing the heated first and second parts together,
adding a third part including a minor portion of triethanolamine to bring the pH to 7.0 and above 7.0, and
adding an aqueous saturated solution of sodium bicarbonate to said first, second and third parts and mixing to provide bicarbonate ions in an emollient carrier having a pH greater than 7.0.

13. A method of making a skin preparation as set forth in claim 12 further including the final adding of mineral oil, alkaline stable fragrance and preservatives.

14. A method as set forth in claim 12 wherein the heated mixture of said first, second, and third parts is stirred until the temperature is down to about 55°–60° C. followed by the addition of said aqueous saturated solution of sodium bicarbonate.

* * * * *